(12) United States Patent
Bruder

(10) Patent No.: US 7,369,639 B2
(45) Date of Patent: May 6, 2008

(54) METHOD AND TOMOGRAPHY UNIT FOR TAKING TOMOGRAPHIC PICTURES OF A BEATING HEART

(75) Inventor: Herbert Bruder, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 122 days.

(21) Appl. No.: 11/349,125

(22) Filed: Feb. 8, 2006

(65) Prior Publication Data

US 2006/0188058 A1    Aug. 24, 2006

(30) Foreign Application Priority Data

Feb. 9, 2005   (DE)   ................ 10 2005 005 916

(51) Int. Cl.
   *G21N 23/083*   (2006.01)
   *A61B 6/00*     (2006.01)

(52) U.S. Cl. ............................. 378/8; 378/95; 600/428
(58) Field of Classification Search .................... 378/8, 378/95; 600/428
See application file for complete search history.

(56) References Cited

U.S. PATENT DOCUMENTS

| 1,688,675 | A | * | 10/1928 | Weyl ........................... 378/95 |
| 2,152,045 | A | * | 3/1939  | Mercer ........................ 335/61 |
| 2,190,389 | A | * | 2/1940  | Siegmund et al. ............. 378/95 |
| 4,739,766 | A | * | 4/1988  | Riederer ...................... 600/413 |
| 4,903,704 | A |   | 2/1990  | Van Eggermond et al. |
| 5,459,769 | A | * | 10/1995 | Brown ........................... 378/4 |
| 5,857,970 | A | * | 1/1999  | Purdy ........................... 600/413 |
| 6,438,196 | B1 | * | 8/2002 | Cesmeli ........................ 378/8 |
| 6,771,999 | B2 | * | 8/2004 | Salla et al. .................. 600/413 |
| 6,792,066 | B1 | * | 9/2004 | Harder et al. ................. 378/4 |
| 6,865,248 | B1 | * | 3/2005 | Rasche et al. ................. 378/8 |
| 2003/0152189 | A1 | * | 8/2003 | Li et al. ...................... 378/8 |
| 2004/0077941 | A1 | * | 4/2004 | Reddy et al. ................. 600/428 |
| 2004/0081269 | A1 | * | 4/2004 | Pan et al. ..................... 378/4 |
| 2005/0065430 | A1 | * | 3/2005 | Wiethoff et al. ............. 600/413 |

FOREIGN PATENT DOCUMENTS

| DE | 28 13 830 | 10/1978 |
| DE | 34 03 334 A1 | 8/1984 |
| WO | WO 01/66011 A2 | 9/2001 |

OTHER PUBLICATIONS

Th. Flohr, B.Ohnesorge: "Heart Rate Adaptive Optimization of Spatial and Temporal Resolution for Electrocardiogram-Gated Multislice Spiral CT of the Heart", Journal of Computer Assisted Tomography, vol. 25, No. 6, 2001, S.907-923.

* cited by examiner

*Primary Examiner*—Edward J. Glick
*Assistant Examiner*—Thomas R. Artman
(74) *Attorney, Agent, or Firm*—Harness, Dickey & Pierce, P.L.C.

(57) ABSTRACT

A method and a tomography unit are disclosed for taking tomographic pictures of a patient's beating heart, in particular X-ray CT pictures. In such a method and tomography unit, only detector data or image data of a portion of the cardiac phase from one or more heart beats is used for taking a picture. Further, at least one pressure signal, produced by the mechanical cardiac pulse and varying temporally with the cardiac cycle, is used for determining the cardiac phase.

26 Claims, 1 Drawing Sheet

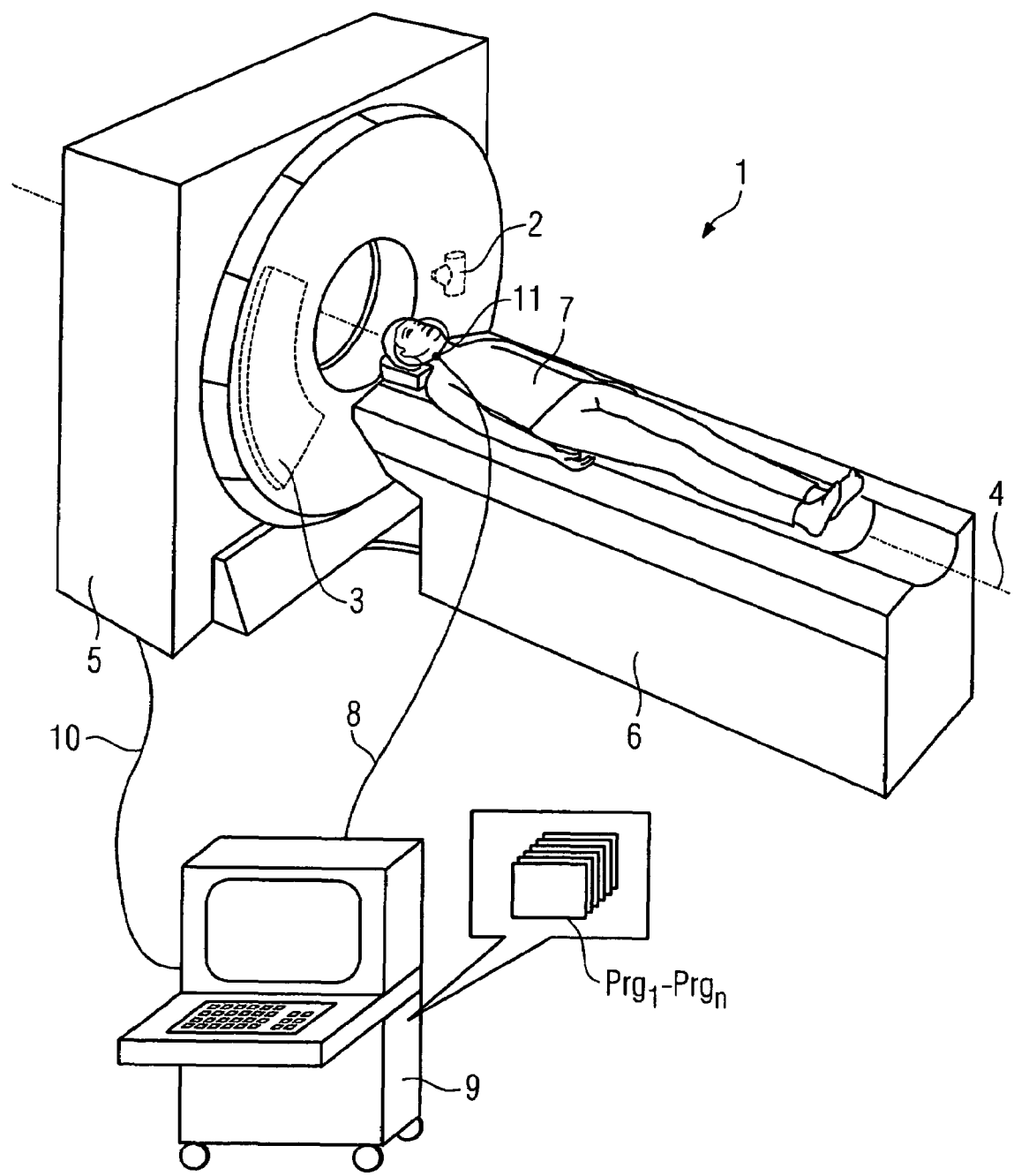

METHOD AND TOMOGRAPHY UNIT FOR TAKING TOMOGRAPHIC PICTURES OF A BEATING HEART

The present application hereby claims priority under 35 U.S.C. §119 on German patent application number DE 10 2005 005 916.3 filed Feb. 9, 2005, the entire contents of which is hereby incorporated herein by reference.

FIELD

The invention generally relates to a method and/or a tomography unit for taking tomographic pictures. For example, it may relate to taking X-ray CT images of a patient's beating heart. Further, it may relate to a method or apparatus wherein only detector data or image data of a portion of the cardiac phase from one or more heart beats is used to take a picture.

BACKGROUND

Similar methods are generally known. When taking computed tomography images, for example, during scanning of the beating heart, ECG signals are picked up and a rest phase of the heart is selected on the basis of the ECG signals, in particular the R wave in the ECG signal. In addition, use is made exclusively of detector data or image data from this cycle phase which are assembled over a number of heart beats such that images of good quality can be reconstructed or put together therefrom.

Problems in the use of ECG signals for determining a rest phase of the heart can occur, for example, when the described ECG exhibits no typical shape because of stimulus conduction disturbances or surviving infarcts such that there can be problems in automatically or manually selecting the correct phase section.

It is true in the meantime, that methods have also been proposed in the case of which the current condition of movement of the heart can be inferred from the detector information. However, this requires the patient to be scanned during the entire cardiac cycle, thus giving rise to a relatively high radiation load for the patient, at least during computed tomography examinations.

SUMMARY

It is therefore an object of at least one embodiment of the invention to find an alternative, triggered cardiotomography method that on the one hand dispenses with ECG signals, and also ideally has an improved or even optimal dose usage.

The inventor has realized that it is possible, even in the case of tomographic examination methods of the beating heart, to use the mechanical pulse information of the circulation of the blood in the way used similarly for fitness machines in order to determine the heart rate. The use of such mechanical pulse information additionally has the advantage that possible phase shifts resulting from the stimulus conduction and a subsequent mechanical reaction of the heart are suppressed. If the pressure pulses measured for this purpose are picked off as close to the heart as possible, for example in the shape of scanning a carotid pulse, the pulse-shifting influence of the mechanical transmission of the pulse from the heart to the respective site of the measurement in the vicinity of an artery is also minimized.

There is also the possibility of using this pulse information additionally in order to initiate triggering of the tube current when a computed tomography system is being used. Moreover, if a phase shift between the measurement site and the site under inspection is feared because of an excessively large distance between the measurement point and heart, during a test bolus injection of contrast medium, there is additionally an empirical determination of the respectively actually occurring phase shift between the pressure pulse at the measurement point and the rest phase optimally situated from the measurement.

According to this basic idea of at least one embodiment of the invention, the inventor proposes to improve the method known per se for taking tomographic pictures of a patient's beating heart, in particular X-ray CT pictures, in the case of which only detector data or image data of a portion of the cardiac phase from one or more heart beats are used for taking a picture to the effect that at least one pressure signal produced by the mechanical cardiac pulse and varying temporally with the cardiac cycle is used for determining the cardiac phase.

The pressure signal may be detected, for example, by a pressure sensor at arteries near the surface. Although it is also possible in principle to carry out the pressure measurement "bloodily", this is an invasive method that unpleasantly stresses the patient. Thus, a "bloodless" measurement through simply putting a pressure sensor onto the surface of the skin appears fundamentally more favorable.

It is also advantageous to take account of the travel time of the pressure pulse from the heart to the site of the pressure measurement when determining the cardiac phase, it appearing to be most favorable, however, to undertake the pulse measurement as close as possible to the heart, for example by using the carotid pulse in the throat region.

Another example possibility of at least one embodiment resides in taking of the pulse at the ear lobe, such as is customary, for example, with the pulse sensors of many fitness machines.

It is possible to make use as pressure sensor of, for example, a piezoelement, put on the patient's skin, which converts the pressure change produced by the pulsing artery into electric signals that it passes on to an appropriate recording system.

As already mentioned, the pulse measurement can also be used to modulate the tube current of an X-ray tube of an examining CT system, this being done as a function of cardiac phase.

It is particularly favorable in the case of the method according to at least one embodiment of the invention when a test scan for determining the subphase to be used optimally in relation to the measured pressure pulse signal is carried out before the actual cardioscan. It is possible thereby to carry out the test scan over a few cardiac phases, for example over a subregion of the heart, but while measuring the entire cardiac cycle, for example with a slight and brief dose of contrast medium, and the most favorable cardiac cycle phase range relative to the currently measured mechanical pulse is determined with the aid of the quality differences between a number of pictures from different cardiac cycle phase ranges.

It is possible, for example, to use the image sharpness as quality feature of the picture, since pictures exhibit only a very slight motional blurring during the rest phase of the heart, while pictures during the movement phase of the heart convey a strong motional blurring. However, it is also possible in this case to determine the movement situation directly from the detector data, as has already been proposed, for example, for some cardio CT examinations. If this method is applied, it is advantageous here that the irradiation takes place during the entire cardiac cycle exclusively in the test phase, and that a high radiation dose level continues to be used during the actual cardiac scan following thereupon only in the rest phase. A further possibility for determining the favorable subcycle consists in examining the correlation coefficients of temporally neighboring pictures over the cardiac cycle, and selecting an instant in the cardiac cycle that exhibits the highest correlation with temporally neighboring pictures.

In principle, the outlined method can be used both with magnetic resonance tomography methods and with computed tomography methods, it being possible to use both spiral scanning and sequential scanning for the computed tomography methods.

Moreover, the method according to at least one embodiment of the invention can be used both wherever incomplete detector data are combined to shape complete detector data from a number of cardiac cycles, and image data are subsequently reconstructed, and also in the case of methods that reconstruct incomplete detector data to shape incomplete image data from a number of cardiac cycles and subsequently combine them to shape complete image data. Both methods have been adequately described in the literature.

According to the methods outlined above, the inventor also proposes a tomography unit for taking three dimensional pictures of a patient's beating heart, for example X-ray CT pictures, having a device for scanning a patient, for example at least one X-ray tube/detector system, and a device, for example an arithmetic unit with programs and program modules, for reconstructing the three-dimensional pictures from detector data of a portion of the cardiac phase from one or more heart beats, in which for the purpose of improvement an apparatus for pressure pulse detection is connected to the device for reconstructing three-dimensional pictures of the beating heart, the cardiac phase being calculated from the mechanical pressure pulse.

If the tomography unit is a computed tomography unit, it is additionally proposed that the apparatus for pressure pulse detection is connected to an apparatus for controlling the tube current of the X-ray tube, and at least one aspect/method/device, for example programming, is provided that trigger the magnitude of the tube current by the pressure pulse.

It is proposed, furthermore, that the tomography unit has an arithmetic and control unit containing programs that carry out the method steps according to at least one embodiment of the invention during operation.

BRIEF DESCRIPTION OF THE DRAWINGS

Aspects of the invention are described in more detail below with reference to an example embodiment with the aid of a single FIGURE, the following reference symbols being used: 1: computed tomography system; 2: X-ray tubes; 3: detector; 4: system axis; 5: housing; 6: displaceable patient couch; 7: patient; 8: pulse measuring lead; 9: control and arithmetic unit; 10: control and data line; 11: pressure sensor; $Prg_x$: computer programs.

FIG. 1 shows an illustration of an example computed tomography for carrying out the method according to at least one embodiment of the invention.

DETAILED DESCRIPTION OF THE EXAMPLE EMBODIMENTS

FIG. 1 shows a computer tomograph 1 having a housing 5 in which there are located a gantry with a circularly revolving X-ray tube 2 and a multirow detector 3 situated opposite. Also illustrated is a patient 7 who is lying on a patient couch 6 and is moved into the opening of the CT 1 for the scanning operation. During the scanning operation, in which the X-ray tube moves in a circle around the patient, a relative movement of the patient in the direction of the system axis 4 can take place such that the spiral scanning takes place relative to the patient, or the patient can also be scanned by being pushed forward sequentially during a scanning pause in many purely circular movements of the tube relative to the patient. The computer tomograph 1 is controlled by the control and arithmetic unit 9 via the control and data line 10.

The data collected by the detector 3 are also transmitted to the computer via the control and data line 10. The control and arithmetic unit 9 has an internal memory and arithmetic processors via which the programs $Prg_1$ to $Prg_n$ for controlling the computer tomograph and for evaluating the collected data are executed. Moreover, a keyboard for data input and a monitor for displaying data are connected to the arithmetic unit.

Also integrated in the control and arithmetic unit 9 is an apparatus for taking up the electric signals of the pressure sensor 11, via which the patient's mechanical pulse is picked up, here from the carotid pulse in the throat region, for example. This then results in a triggering of the scan and, if appropriate, also of the tube currents in the way described above.

It may be pointed out in addition to this that tomographic pictures within the meaning of at least one embodiment of the invention are to be understood as all known variants relating to the three-dimensional display, for example, the reconstruction of tomograms, also the reconstruction of volume data records or the voxelwise reconstruction.

It goes without saying that the abovementioned features of at least one embodiment of the invention can be used not only in the respectively specified combination, but also in other combinations or on their own, without departing from the scope of the invention.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for taking a tomographic picture of a patient's beating heart, comprising:
   taking a tomographic picture using only data of a portion of a cardiac phase from at least one heart beat,
   using at least one pressure signal, produced by a mechanical pulse and varying temporally with a cardiac cycle, for determining a cardiac phase, and
   taking a test scan for determining a subphase to be used in relation to the at least one pressure signal, for carrying out a cardioscan.

2. The method as claimed in claim 1, wherein the at least one pressure signal is detected by a pressure sensor at arteries near the surface.

3. The method as claimed in claim 2, wherein account is taken of a travel time of the at least one pressure signal from a heart to a site of a pressure measurement when determining the cardiac phase.

4. The method as claimed in claim 2, wherein a piezo-element put on a patient's skin is used as the pressure sensor.

5. The method as claimed in claim 1, wherein a carotid pulse in the throat region is used for measuring the mechanical pulse.

6. The method as claimed in claim 1, wherein the mechanical pulse is measured at the ear lobe.

7. The method as claimed in claim 1, wherein the at least one pressure signal is used for modulating the tube current of an X-ray tube of an examining CT system, this being done as a function of the cardiac phase.

8. The method as claimed in claim 1, wherein the test scan is carried out over a few cardiac phases, but while measuring the entire cardiac cycle, and a most favorable cardiac cycle phase range relative to the currently measured mechanical pulse is determined with the aid of quality differences between a number of pictures from different cardiac cycle phase ranges.

9. The method as claimed in claim 1, wherein the method is used in conjunction with a magnetic resonance, tomography method.

10. The method as claimed in claim 9, wherein incomplete detector data from a number of cardiac cycles are combined to shape complete detector data, and image data are subsequently reconstructed.

11. The method as claimed in claim 1, wherein the method is used in conjunction with an X-ray computed tomography method.

12. The method as claimed in claim 11, wherein the method is used in conjunction with spiral scanning.

13. The method as claimed in claim 11, wherein the method is used in conjunction with sequential scanning.

14. The method as claimed in claim 1, wherein incomplete detector data from a number of cardiac cycles are reconstructed to shape incomplete image data and are subsequently combined to shape complete image data.

15. A tomography unit comprising an arithmetic and control unit, including programs and processes during operation, which executes the steps of claim 1.

16. The method as claimed in claim 1, wherein the tomographic picture is an X-ray CT picture.

17. The method as claimed in claim 1, wherein the test scan is carried out over a subregion of the heart, but while measuring the entire cardiac cycle with a slight and brief dose of contrast medium, and a most favorable cardiac cycle phase range relative to the currently measured mechanical pulse is determined with the aid of quality differences between a number of pictures from different cardiac cycle phase ranges.

18. A tomography unit for taking a tomographic picture of a patient's beating heart, comprising:
   means for scanning a patient;
   means for reconstructing three-dimensional pictures from detector data of a portion of a cardiac phase from one or more heart beats;
   means for pressure pulse detection, connected to the means for reconstructing three-dimensional pictures of a beating heart, the cardiac phase being calculated from at least one pressure pulse detected; and
   means for taking a test scan for determining a subphase to be used in relation to the at least one pressure pulse, for carrying out a cardioscan.

19. An X-ray computed tomography unit as claimed in claim 18, wherein the means for pressure pulse detection is connected to an apparatus for controlling a tube current of an X-ray tube, and wherein means are provided that trigger a magnitude of the tube current by the pressure pulse.

20. An X-ray computed-tomography unit as claimed in claim 18, wherein the means for scanning a patient includes at least one X-ray tube/detector system, and wherein the means for reconstructing includes an arithmetic unit with at least one of programs and program modules.

21. The X-ray computed tomography unit as claimed in claim 18, wherein the tomographic picture is an X-ray CT picture.

22. A method for taking a tomographic picture of a patient's beating heart, comprising:
   using at least one pressure pulse, produced by a mechanical cardiac pulse and varying temporally with the cardiac cycle, for determining a cardiac phase;
   taking a tomographic picture using only detector data or image data of a portion of the cardiac phase from one or more heart beats; and
   taking a test scan for determining a subphase to be used in relation to the at least one pressure pulse, for carrying out a cardioscan.

23. The method as claimed in claim 22, wherein the tomographic picture is an X-ray CT picture.

24. The method as claimed in claim 23, wherein account is taken of a travel time of the at least one pressure pulse from a heart to a site of a pressure measurement when determining the cardiac phase.

25. The method as claimed in claim 22, wherein the at least one pressure pulse is detected by a pressure sensor at arteries near the surface.

26. A tomography unit for taking a tomographic picture of a patient's beating heart, comprising:
   a reconstructing device to form three-dimensional pictures from detector data of a portion of a cardiac phase from one or more heart beats;
   a scanning device, connected to the reconstructing device; and
   a pressure pulse detection device, connected to the reconstructing device, the cardiac phase being calculated from a pressure pulse detected by the pressure pulse detection device, wherein a test scan, for determining a subphase to be used in relation to the pressure pulse, is carried out for a cardioscan.

* * * * *